United States Patent
Bruggemann et al.

(10) Patent No.: US 9,265,906 B2
(45) Date of Patent: Feb. 23, 2016

(54) COMPRESSIBLE CANNULA CONNECTOR WITH RELEASE GRIP

(71) Applicant: Covidien LP, Mansfield, MA (US)

(72) Inventors: Martin J. Bruggemann, Dublin (IE); James M. Ryan, Dublin (IE); Declan Kiernan, Co. Longford (IE); Alan Finneran, Co. Offaly (IE); Seamus P. Maguire, Athlone (IE)

(73) Assignee: COVIDIEN LP, Mansfield, MA (US)

( * ) Notice: Subject to any disclaimer, the term of this patent is extended or adjusted under 35 U.S.C. 154(b) by 321 days.

(21) Appl. No.: 13/776,194

(22) Filed: Feb. 25, 2013

(65) Prior Publication Data

US 2014/0238389 A1 Aug. 28, 2014

(51) Int. Cl.
*A61M 11/00* (2006.01)
*A61M 16/04* (2006.01)

(52) U.S. Cl.
CPC ....... *A61M 16/0427* (2014.02); *A61M 16/0434* (2013.01); *A61M 16/0465* (2013.01); *A61M 16/0488* (2013.01); *A61M 16/0497* (2013.01); *A61M 2205/583* (2013.01)

(58) Field of Classification Search
CPC ............ A61M 39/12; A61M 16/0465; A61M 16/0427; A61M 2039/1027; A61M 39/1011; A61M 39/10; A61M 16/04; A61M 16/0816; A61M 25/0014; A61M 16/0488; A61M 16/0434; A61M 16/0497; A61M 2205/583
USPC ........................................ 128/207.14–207.17
See application file for complete search history.

(56) References Cited

U.S. PATENT DOCUMENTS

| | | | |
|---|---|---|---|
| 3,169,529 A | 2/1965 | Koenig |
| 3,225,767 A | 12/1965 | Smith |
| 3,948,273 A | 4/1976 | Sanders |
| 4,315,505 A | 2/1982 | Crandall et al. |
| 4,817,598 A | 4/1989 | LaBombard |
| 4,909,248 A | 3/1990 | McLennan |
| 5,386,826 A | 2/1995 | Inglis et al. |
| 5,762,638 A | 6/1998 | Shikani et al. |
| 5,864,938 A | 2/1999 | Gansel et al. |
| 5,996,582 A | 12/1999 | Turnbull |
| 6,019,753 A | 2/2000 | Pagan |
| 6,024,730 A | 2/2000 | Pagan |

(Continued)

FOREIGN PATENT DOCUMENTS

| WO | WO2008046418 A1 | 4/2008 |
|---|---|---|
| WO | 2011149664 A1 | 12/2011 |
| WO | 2012064479 A2 | 5/2012 |

OTHER PUBLICATIONS

Lazarus medical; Securing Critical Connections—Phoneris inner Cannulae and Phoneris AeroFlex—5011 Rev. 2; 5006 Rev. 3, no date.

(Continued)

*Primary Examiner* — Steven Douglas
(74) *Attorney, Agent, or Firm* — Fletcher Yoder PC

(57) ABSTRACT

A tracheal tube assembly includes an outer cannula configured to be positioned in a patient airway and an inner cannula configured to be disposed inside the outer cannula. The tracheal tube assembly further includes a flange member secured about the outer cannula, and an outer cannula connector coupled to a proximal end of the outer cannula. The outer cannula connector includes a compressible portion may be compressed while inserting or removing the inner cannula.

22 Claims, 8 Drawing Sheets

(56) References Cited

U.S. PATENT DOCUMENTS

| | | | |
|---|---|---|---|
| 6,105,577 A | 8/2000 | Varner | |
| 6,135,110 A | 10/2000 | Roy | |
| 6,248,099 B1 | 6/2001 | Bell | |
| 6,588,426 B2* | 7/2003 | Linderoth | 128/207.14 |
| D479,876 S | 9/2003 | Gradon et al. | |
| 6,679,871 B2 | 1/2004 | Hahnen | |
| 6,722,367 B1 | 4/2004 | Blom | |
| 6,725,862 B2 | 4/2004 | Klinberg et al. | |
| 6,739,339 B2 | 5/2004 | Bergamaschi | |
| 6,796,309 B2 | 9/2004 | Nash et al. | |
| 6,840,242 B1 | 1/2005 | McCoy | |
| 7,086,402 B2 | 8/2006 | Peterson | |
| 7,156,090 B2 | 1/2007 | Nomori | |
| 7,305,989 B2 | 12/2007 | Gostelow | |
| 7,341,061 B2 | 3/2008 | Wood | |
| D585,980 S | 2/2009 | Cabrera | |
| 7,681,576 B2 | 3/2010 | Thomas et al. | |
| 7,987,851 B2* | 8/2011 | Blom et al. | 128/207.16 |
| 8,127,766 B2 | 3/2012 | Chang | |
| 2004/0068278 A1 | 4/2004 | Fleischman et al. | |
| 2004/0154623 A1 | 8/2004 | Schaeffer et al. | |
| 2004/0177851 A1 | 9/2004 | Acosta | |
| 2005/0066816 A1 | 3/2005 | Wright | |
| 2005/0166924 A1 | 8/2005 | Thomas et al. | |
| 2005/0241643 A1 | 11/2005 | Webber | |
| 2006/0070628 A1 | 4/2006 | Byatt et al. | |
| 2006/0081254 A1 | 4/2006 | Gostelow | |
| 2006/0124134 A1 | 6/2006 | Wood | |
| 2007/0012317 A1 | 1/2007 | Flagler et al. | |
| 2007/0181130 A1* | 8/2007 | Worley | 128/207.14 |
| 2007/0246051 A1 | 10/2007 | Newman | |
| 2007/0255258 A1 | 11/2007 | Matlock et al. | |
| 2008/0072911 A1 | 3/2008 | Flagler et al. | |
| 2008/0142001 A1 | 6/2008 | Wright | |
| 2008/0142003 A1 | 6/2008 | Depel | |
| 2008/0149108 A1 | 6/2008 | Neame | |
| 2008/0216839 A1 | 9/2008 | Rutter | |
| 2008/0257353 A1 | 10/2008 | Yamamoto et al. | |
| 2009/0025717 A1 | 1/2009 | Pinel | |
| 2009/0145440 A1 | 6/2009 | Bierman et al. | |
| 2010/0089403 A1 | 4/2010 | Solly | |
| 2010/0244432 A1 | 9/2010 | Neame et al. | |
| 2010/0307488 A1 | 12/2010 | Poulsen et al. | |
| 2010/0319705 A1 | 12/2010 | Thomas et al. | |
| 2011/0083672 A1 | 4/2011 | Webster et al. | |
| 2012/0103341 A1 | 5/2012 | Behlmaier | |

OTHER PUBLICATIONS 204A extra-long speaking tube, type B; http://www.kapitex.com/tracheostomy/tracoecomfort/tracoecomfort-204a/, no date.

sales@bryanmedical.net; TRACOE TWIST ref 304 http://www.bryanmedical.net/Tracoe/Tracoe_Twist304.html, no date.

Portex Tracheostomy Care Hanbook, no date.

Portex Uniperc Tube Brochure 2, no date.

U.S. Appl. No. 29/428,717, filed Aug. 2, 2012, Bruggemann et al.

U.S. Appl. No. 29/428,719, filed Aug. 2, 2012, Bruggemann et al.

U.S. Appl. No. 13/565,273, filed Aug. 12, 2013, Bruggemann et al.

Rusch Crystal (2010) http://www.teleflexmedical.com/prod_rusch.php.

Percutan (2010) http://www.tracoe.com/products.html.

Pure (2010) http://www.tracoe.com/products.html.

Twist (2010) http://www.tracoe.com/products.html.

Mini (2010) http://www.tracoe.com/products.html.

Comfort (2010) http://www.tracoe.com/products.html.

Rusch Tracheoflex (2010) http://www.teleflexmedical.com/prod_rusch.php.

Silicone Air Cuff Tracheostomy Tubes, Pediatric & Neonatal TT, Adjustable Neck Flange TT; (2010) http://www.arcadiamedical.com/arcadia/main.asp?cid=4&pid=2.

Silicone Cuffless Adult Tracheostomy Tubes; (2010) http://www.arcadiamedical.com/arcadia/main.asp?cid=4&pid=2.

Bivona Adult Fome-Cuf (2013) http://www.smiths-medical.com/catalog/endotracheal-tubes.

Bivona Aire-Cuf Neonatal and Pediatric (2013) http://www.smiths-medical.com/catalog/endotracheal-tubes.

Portex Blue Line Cuffed (2013) http://www.smiths-medical.com/catalog/endotracheal-tubes.

Portex Blue Line Uncuffed (2013) http://www.smiths-medical.com/catalog/endotracheal-tubes.

Bjorling et al., "Clinical Use and Material Wear of Polymeric Tracheostomy Tubes", Laryngoscope 117: Sep. 2007.

Liu, et al., "Extra-long Montgomery T Tube in Major Airway Stenosis", The Journal of Laryngology & Otology (2008), 123, 772-777.

U.S. Appl. No. 29/428,717 file history, no date.

U.S. Appl. No. 29/428,719 file history, no date.

U.S. Appl. No. 13/565,273 file history, no date.

U.S. Appl. No. 13/565,273, filed Aug. 12, 2012, Martin J. Bruggemann.

International Search Report and Written Opinion for PCT Application No. PCT/US2013/052867 dated Dec. 26, 2013; 7 pgs.

* cited by examiner

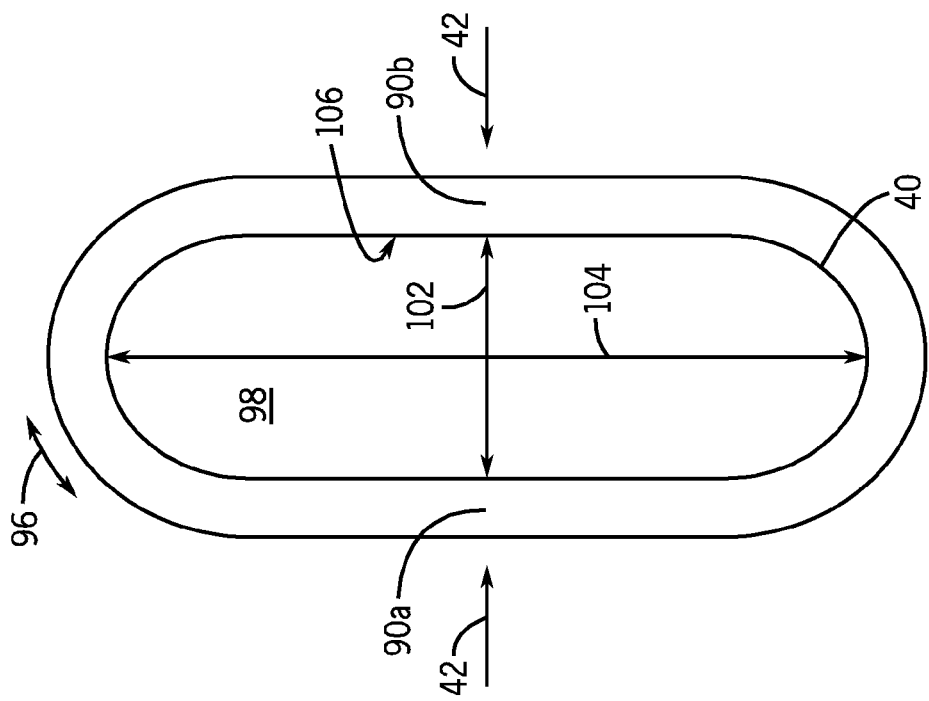
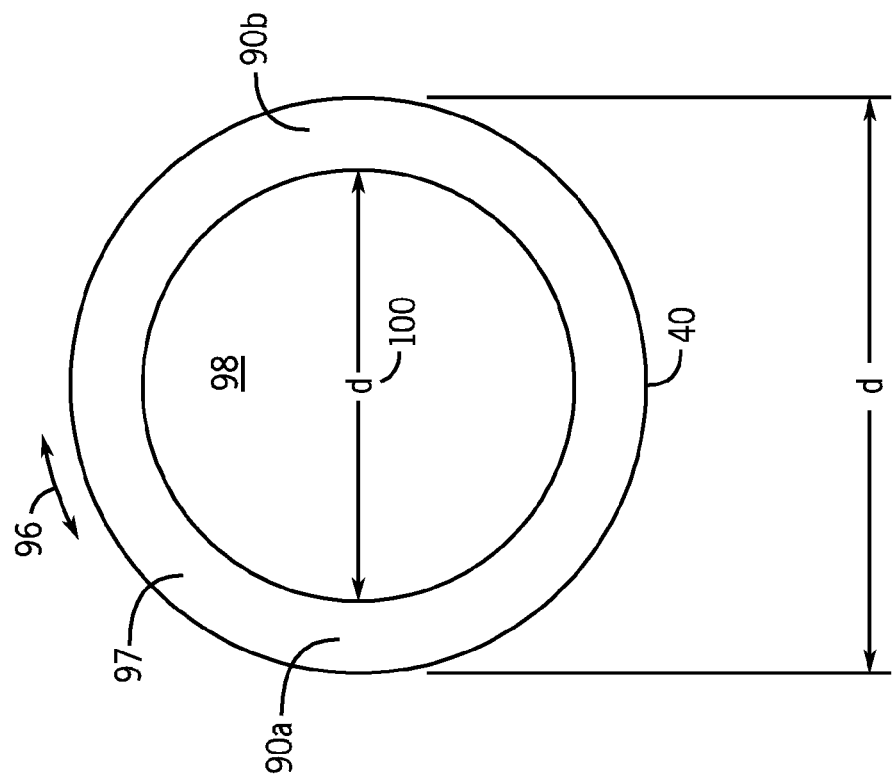

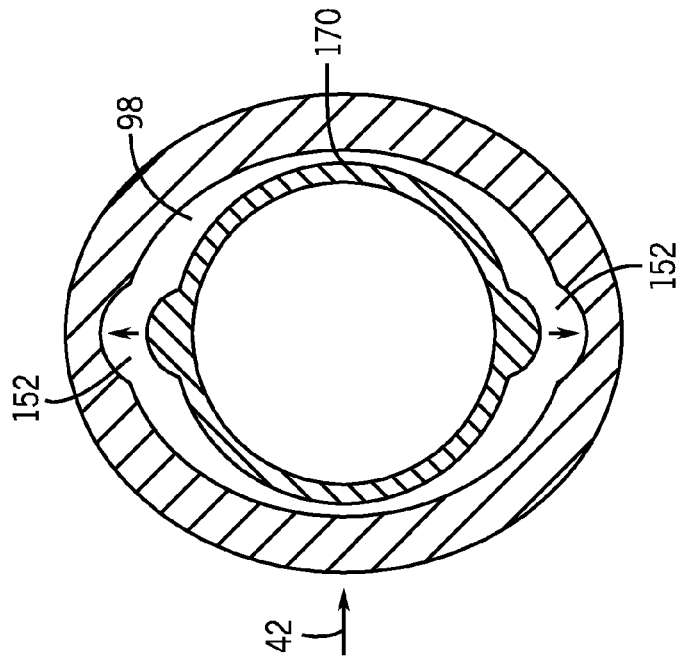
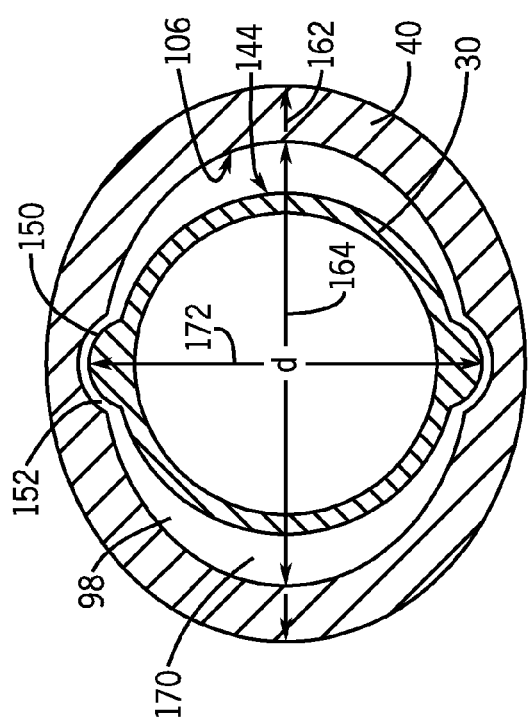
FIG. 6A
FIG. 6B

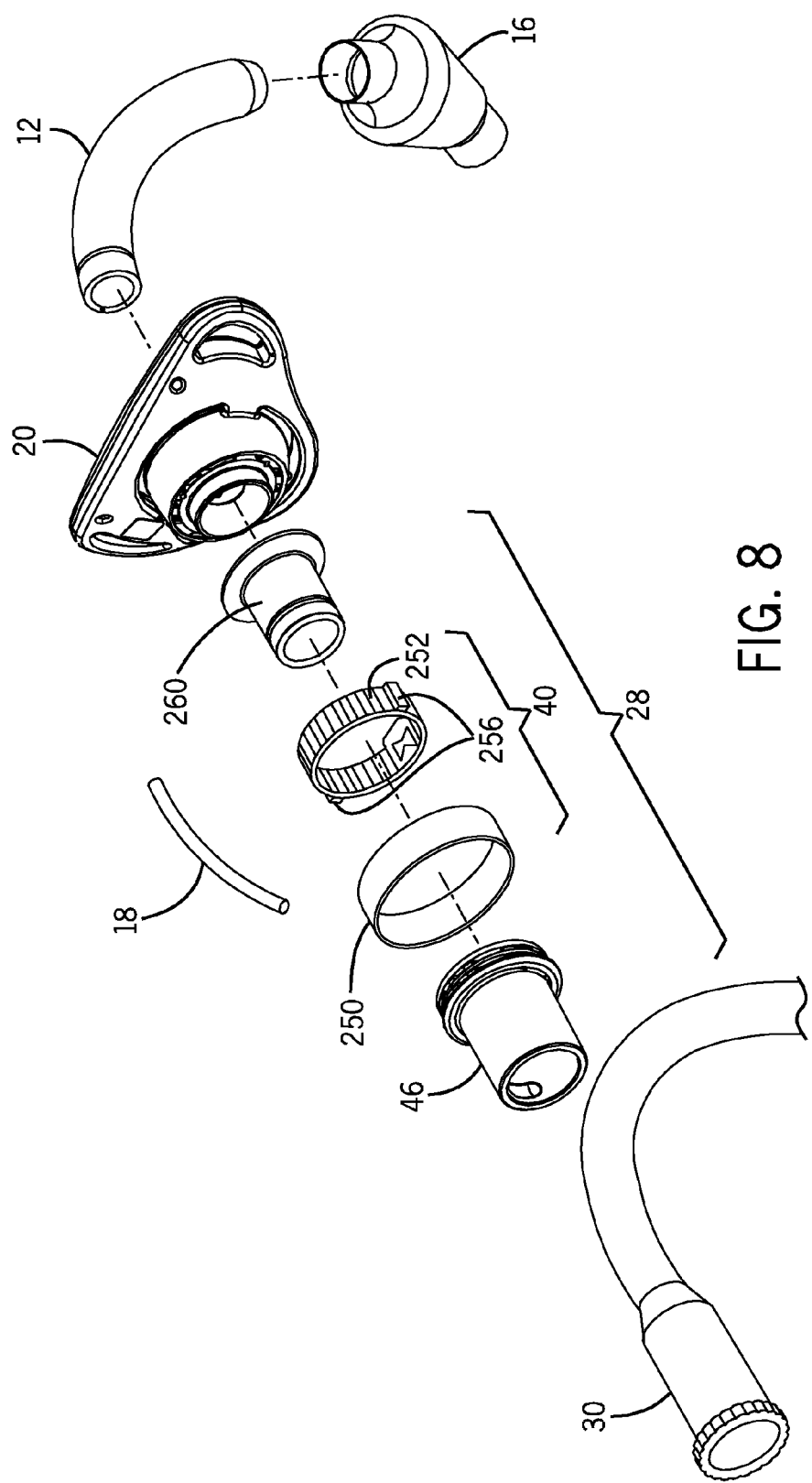

COMPRESSIBLE CANNULA CONNECTOR WITH RELEASE GRIP

BACKGROUND

The present disclosure relates generally to the field of tracheal tubes and, more particularly, to a tracheal tube including a compressible outer cannula with a release grip.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

A wide variety of situations exist in which artificial ventilation of a patient may be desired. For short-term ventilation or during certain surgical procedures, endotracheal tubes may be inserted through the mouth to provide oxygen and other gasses to a patient. For other applications, particularly when longer-term intubation is anticipated, tracheostomy tubes may be preferred. Tracheostomy tubes are typically inserted through an incision made in the neck of the patient and through the trachea. A resulting stoma is formed between the tracheal rings below the vocal chords. The tracheostomy tube is then inserted through the opening. In general, two procedures are common for insertion of tracheostomy tubes, including a surgical procedure and a percutaneous technique.

Such tubes may include an inner cannula, such as a reusable inner cannula, or a disposable inner cannula. The inner cannula may be disposed inside the tracheostomy tube and used as a conduit for liquids or gas incoming and outgoing into the patient's lungs. The inner cannula may be removed for cleaning and for disposal of secretions without disturbing the placement of the tracheostomy tube. A connector is typically provided at an upper or proximal end where the tube exits the patient airway, suitable for coupling the ventilator with the inner cannula. In one embodiment, the inner cannula may be removed, cleaned, and reused. In another embodiment, the inner cannula may be disposable, and a new inner cannula may then be positioned inside of the tracheal tube. By enabling the cleaning and/or replacement of the inner cannula, a ventilation circuit may be kept clean and free of secretions.

Standard connectors have been developed to allow the tracheal tube to then be fluidly coupled to artificial ventilation equipment to supply the desired air or gas mixture to the patient, and to evacuate gases from the lungs. One difficulty that arises in the use of tracheal tubes, and tracheostomy tubes in particular, is in the connection of the tube to the ventilation equipment. For example, an inner cannula may not be installed, or may be installed improperly. This may lead to difficulties with ventilation when a connection is made to ventilation equipment.

There is a need, therefore, for improved tracheal tubes, and particularly for improved tracheostomy tubes. It would be desirable to provide a tube that allows for ease of placement and connection of the inner cannula during ventilation.

BRIEF DESCRIPTION

This disclosure provides a novel tracheal tube designed to respond to such needs with a low insertion force and a high retention force. The tracheal tube may be a tube with a separate inner cannula and outer cannula. The outer cannula connector includes a relatively rigid portion (e.g., a standard 15 mm connector) that couples to upstream medical tubing and/or devices. The outer cannula connector also includes a compressible portion that compresses to change the shape and/or diameter of the interior of the outer cannula connector. This in turn facilitates release of an inserted inner cannula. In certain embodiments, the inner cannula may include features that mate with complementary features on the compressible portion. Compression may release the mating features. In contrast to other types of inner cannula connectors, such as threaded or snap-on connectors, the disclosed embodiments may provide inner cannulas that may be inserted and released with low insertion forces. In addition, the inner cannulas may also resist axial or rotational displacement relative to the outer cannula.

Thus, in accordance with a first aspect, a tracheal tube assembly includes an outer cannula configured to be positioned in a patient airway. The assembly further includes a flange member secured about the outer cannula and an outer cannula connector coupled to a proximal end of the outer cannula wherein the outer cannula connector comprises a proximal rigid portion and a distal compressible portion wherein compression of the distal compressible portion results in a larger inner diameter of the compressible portion in at least one dimension. The assembly further includes an inner cannula configured to be disposed inside the outer cannula such that the inner cannula and the outer cannula are coaxial an inner cannula connector coupled to the inner cannula and configured to be disposed in the outer cannula connector.

In accordance with another aspect, a tracheal tube outer cannula includes a conduit configured to receive an inner cannula; a connector coupled to the conduit, the connector comprising: a compressible portion disposed between a proximal portion of the connector and the conduit, wherein the compressible portion is configured to be deformed when compressed along a first axis such that a first diameter along the first axis decreases and a second diameter along a second axis increases relative to an uncompressed configuration.

Also disclosed herein is a tracheal tube assembly that includes an outer cannula configured to be positioned in a patient airway; a flange member secured about the outer cannula; an outer cannula connector coupled to a proximal end of the outer cannula, wherein the outer cannula connector comprises a compressible portion disposed between the flange member and a rigid proximal portion, wherein the compressible portion is configured to be in an uncompressed configuration when unbiased and a compressed configuration when force is applied; an inner cannula configured to be disposed inside the outer cannula such that the inner cannula and the outer cannula are coaxial; and an inner cannula connector coupled to the inner cannula and configured to be disposed in the outer cannula connector.

BRIEF DESCRIPTION OF THE DRAWINGS

Various aspects of the disclosed techniques may become apparent upon reading the following detailed description and upon reference to the drawings in which:

FIG. 4A is a cross-sectional of a compressible portion of the tracheal tube of FIG. 3 in an uncompressed configuration;

FIG. 4B shows the compressible portion of FIG. 4A in the compressed configuration;

FIG. 6A is a cross-sectional of an alternative embodiment of a compressible portion of the tracheal tube of FIG. 3 in an uncompressed configuration with an inserted inner cannula;

FIG. 6B shows the compressible portion of FIG. 6A in the compressed configuration;

FIG. 8 is an exploded view of the tracheal tube of FIG. 1.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The tracheal tubes as provided herein are disposable rather than reusable, capable of providing differential mechanical ventilation to either or both lungs, and capable of supporting all other functions of standard tracheal tubes (e.g. sealing, positive pressure generation, suctioning, irrigation, drug instillation, etc). The tracheal tubes can be used in conjunction with all acceptable auxiliary airway devices such as (e.g. heat and humidity conservers, mechanical ventilators, humidifiers, closed suction systems, scavengers, capnometers, oxygen analyzers, mass spectrometers, PEEP/CPAP devices, etc). Furthermore, although the embodiments of the present disclosure illustrated and described herein are discussed in the context of tracheal tubes such as tracheostomy tubes, it should be noted that presently contemplated embodiments may include a tracheal tube assembly including a compressible release grip used in conjunction with other types of airway devices. For example, the disclosed embodiments may be used in conjunction with a single-lumen tube, an endotracheal tube, a double-lumen tube (e.g., a Broncho-Cath™ tube), a specialty tube, or any other airway device with a main ventilation lumen. Indeed, any device with a ventilation lumen designed for use in an airway of a patient may include an inner cannula with a compressible end as provided. As used herein, the term "tracheal tube" may include an endotracheal tube, a tracheostomy tube, a double-lumen tube, a bronchoblocking tube, a specialty tube, or any other airway device.

Figure 1:
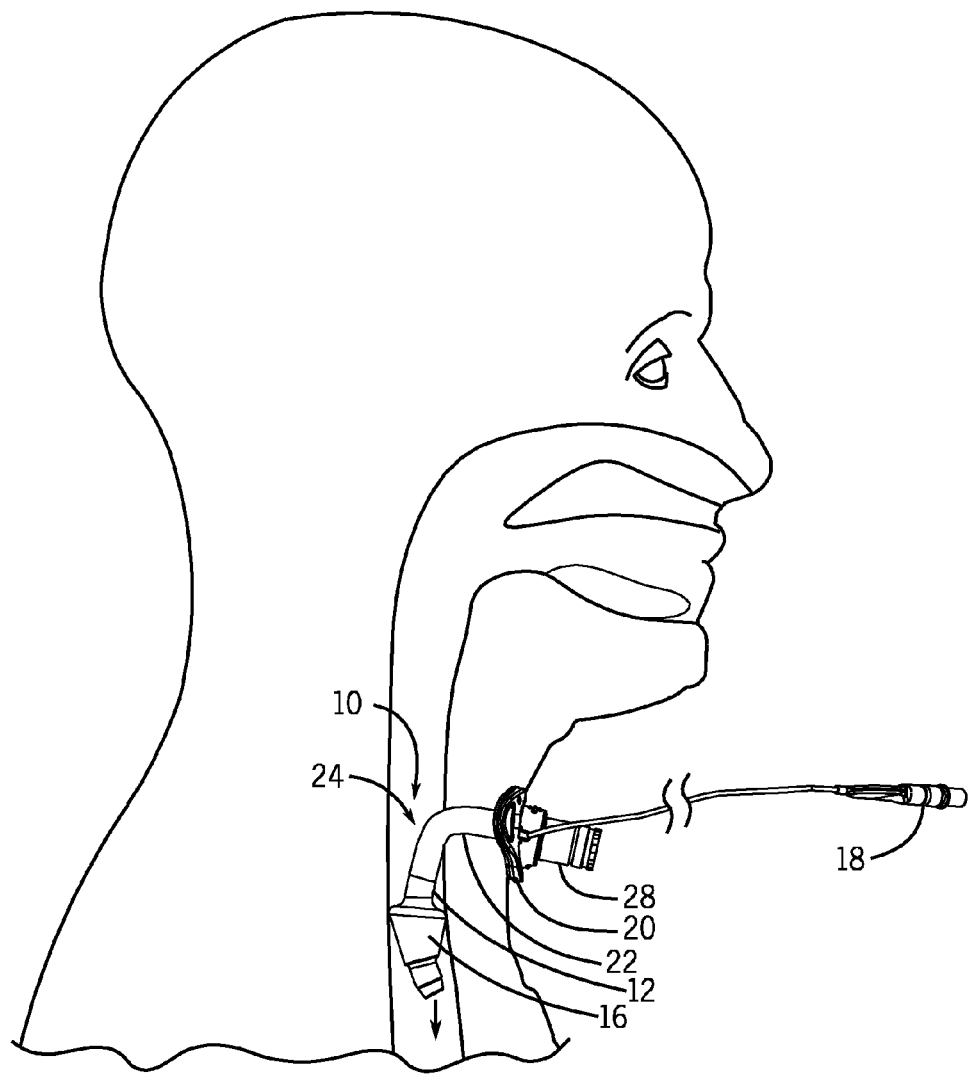
FIG. 1 is a perspective view of a tracheal tube with a compressible inner cannula connector inserted into a patient in accordance with embodiments of the present disclosure.

Turning now to the drawings, FIG. 1 is a perspective view of an exemplary tracheal tube 10 placed in a patient's airway in accordance with aspects of the present disclosure. The tracheal tube assembly 10 represented in the figures is a tracheostomy tube, although aspects of this disclosure could be applied to other tracheal tube structures, such as endotracheal tubes. The application to a tracheostomy tube is apt, however, insomuch as such tubes tend to be worn for longer periods of time and, thus, may include a removable and/or disposable inner cannula disposed inside of an outer cannula 12, which is useful in maintaining a clean ventilation circuit.

The tracheal tube 10 includes an outer cannula 12 that defines a ventilation lumen and that facilitates the transfer of gases to and from the lungs. The tracheal tube 10 includes an inflatable cuff 16 disposed on the outer cannula 12. However, certain embodiments of the disclosure may be used in conjunction with cuffless tubes. A proximal end of the tracheal tube 12 may connect to upstream airway devices (e.g., a ventilator) via the appropriate medical tubing and/or connectors. In embodiments that include a cuff 16, a pilot balloon and inflation line assembly 18 is coupled to the cuff 16.

The outer cannula 12 is illustrated extending both distally as well as proximally from a flange member 20. A pair of side wings of the flange 20 extend laterally and serve to allow a strap or retaining member (not shown) to hold the tube assembly 10 in place on the patient. In one embodiment, apertures formed in each side of the flange member 20 allow the passage of such a retaining device. In many applications, the flange member 20 may be taped or sutured in place as well. During intubation, the tracheal tube assembly 10 is placed through an opening formed in the neck and trachea of a patient and extending into the patient airway. In certain embodiments, the tracheal tube assembly 10 is curved to accommodate the curved tracheal passageway. For example, the outer cannula 12 may be curved in an unbiased state (i.e., outside the patient) such that an inner curve 22 is generally positioned on a ventral side of the patient while the outer curve 24 is positioned on the dorsal side of the patient when the tracheal tube assembly 10 is inserted in the patient. Further, while a distal portion of the outer cannula 12 is inserted within the patient, a proximal portion of the outer cannula 12 forms an outer cannula connector 28. As provided herein, the outer cannula connector 28 includes a compressible portion that may be compressed to facilitate insertion and/or removal of the inner cannula and, in an uncompressed configuration, forms a secure connection.

Figure 2:
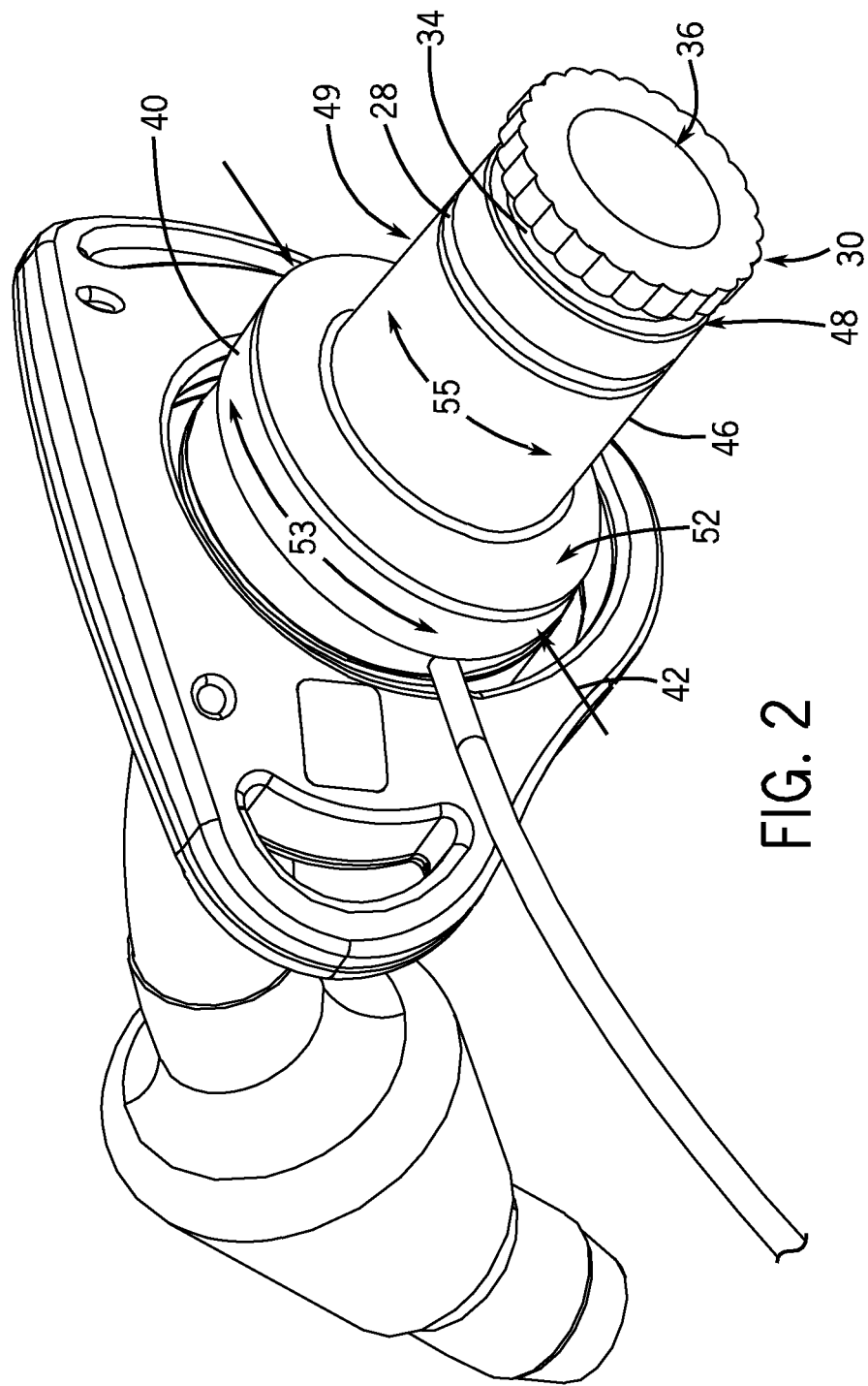
FIG. 2 is a perspective view of the tracheal tube of FIG. 1.

FIG. 2 is a perspective view of the tracheal tube assembly 10 showing an inner cannula 30 inserted in the outer cannula 12 and forming a connection with the outer cannula connector 28. A proximal end 34 of the inner cannula connector 36 is exposed (i.e., is not within the outer cannula connector 28). The inner cannula 30 is generally coaxial with the outer cannula 12 and is shaped to fit within the outer cannula 12 to form the gas conveying passageway to the patient. In this manner, the inner cannula 30 may be removed and replaced while the outer cannula 12 is retained. This reduces stress on the stoma while permitting cleaning of the passageway. The outer cannula connector 28 includes a compressible portion 40. A biasing force (shown by arrows 42) compresses the compressible portion 40 to release the grip and/or connection between the inner cannula 30 and the outer cannula 12.

The outer cannula connector 28 also includes a proximal coupler 46 that forms a connection with upstream medical devices. The outer cannula connector 28 may be formed in accordance with industry standards to permit and facilitate connection to ventilating equipment (not shown). By way of example, the outer cannula connector 28 is a 15 mm connector, although other sizes and connector styles may be used. Additionally, the tracheal tube assembly 10 may be connected to other medical devices, such as a suction device, a T-junction, a medicine delivery system, and so forth. Indeed, the outer cannula connector 28 may enable the attachment of one or more medical devices to the tracheal tube assembly 10. To accommodate such a connection, the inner cannula 30 and its proximal end 34 may be formed such that, when inserted, the inner cannula 30 does not interfere with coupling via the outer cannula connector 28. To that end, in particular embodiments, the widest diameter of the inner cannula 30, including any protruding portions, is smaller than the widest outer diameter (e.g., 15 mm) of the proximal coupler 46. Because the inner cannula 30 is configured to be inserted and/or removed by an operator, the proximal end 34 may protrude from the outer cannula connector 28 to allow the inner cannula 30 to be manipulated. For example, the proximal end 34 of the inner cannula 30 may be positioned so that the operator grips the proximal end 34 during insertion or removal.

The compressible portion 40, which is located away from a proximal end 48 of the inner cannula connector 28, may extend radially away from an exterior surface 49 of the proximal coupler 46. Accordingly, the compressible region 40 may form a shelf 52 that couples the compressible region 40 to the proximal coupler 46. In one embodiment, an outer circumference 53 of the proximal coupler 46 may fit entirely within an outer circumference 54 of the compressible portion 40. In this manner, the relatively larger compressible portion 40 forms a slightly larger passageway with room for compression in at least one direction (e.g., along arrows 42).

Figure 3:
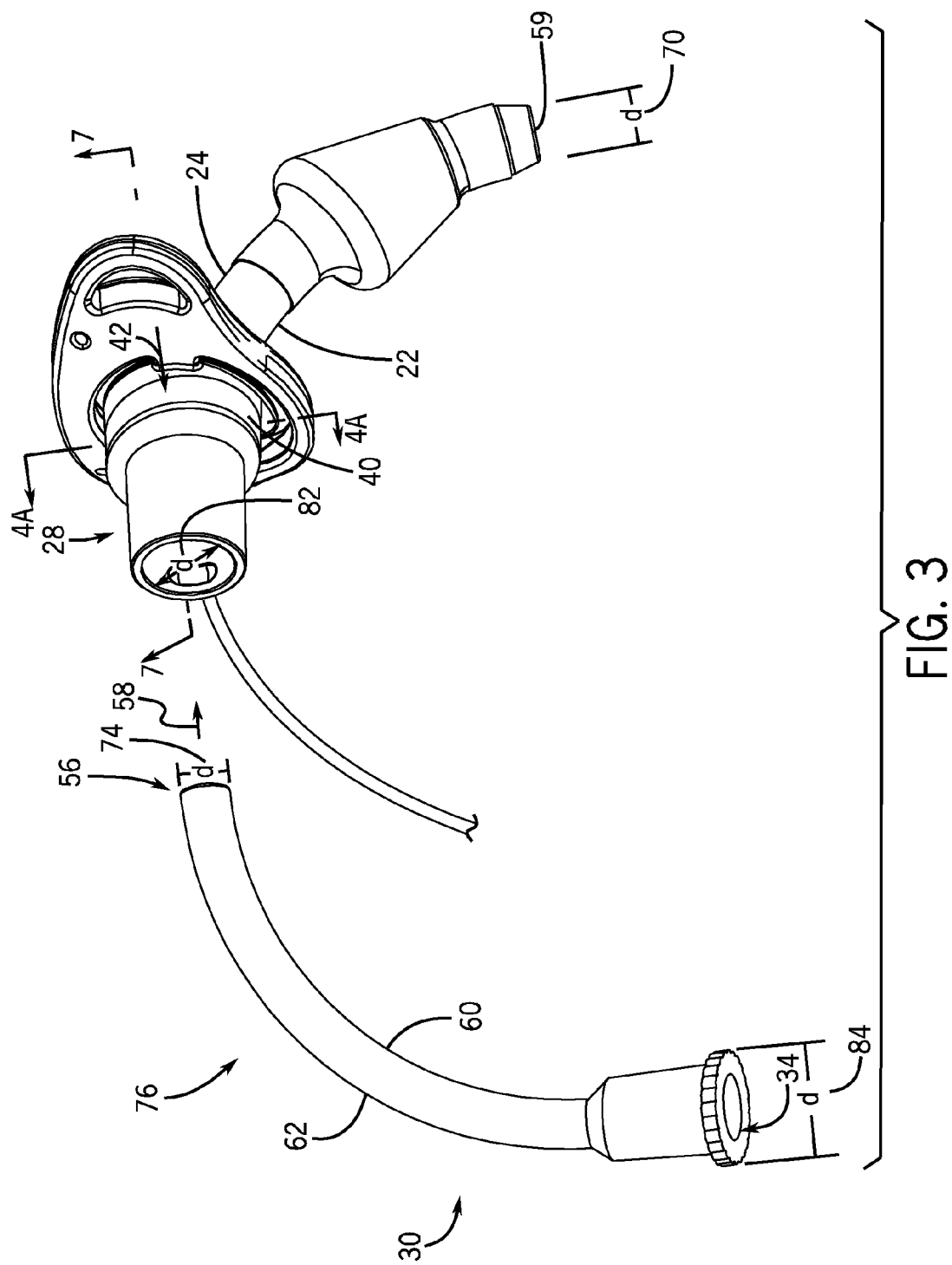
FIG. 3 is a perspective view of the inner cannula outside of the outer cannula of the tracheal tube of FIG. 1.

In operation, the inner cannula 30 may be manually inserted into the outer cannula 12. As shown in FIG. 3, the inner cannula 30 may be inserted by pushing the distal end 56 through the proximal end 34 of the outer cannula 12, e.g., in the direction of arrow 58. The insertion is complete when the distal end 56 is generally located at or near the distal end 59 of the outer cannula 12. In certain embodiments, the distal end 56 of the inner cannula 30 terminates short of the distal end 59 of the outer cannula and is disposed entirely within the outer cannula. When the inner cannula 30 is inserted, the compressible end region 32 is disposed at least in part within the outer cannula connector 28. In embodiments in which the outer cannula forms a curve, such as a Magill curve, the inner cannula 30 may also be curved in a complementary fashion. Accordingly, the insertion may be directional such that proper insertion involves an inner curve 60 of the inner cannula 30 located proximate to or corresponding with the inner curve 22 of the outer cannula 12 (which in turn corresponds to a ventral side of the patient when inserted). Similarly, the outer curve 62 of the inner cannula 30 will be located proximate to the outer curve 24 of the outer cannula 12 (which in turn corresponds to a dorsal side of the patient when inserted). The positioning of the inner cannula 30 in the outer cannula 12 may be facilitated by operator technique and, in particular embodiments, with the aid of markings, instructions, or other visual indicators.

The inner cannula 30 forms a conduit from which liquids or gases, including medications, may enter through the proximal end 34. Both the inner cannula 30 and the outer cannula 12 have dimensions selected to fit easily through the stoma. In practice, a range of such tubes may be provided to accommodate the different contours and sizes of patients and patient airways. Such tube families may include tubes designed for neonatal and pediatric patients as well as for adults. By way of example only, the outer cannula 12 of the tube 10 may range from 4 mm to 16 mm. The inner cannula 30 may be sized to correspond with an appropriate outer cannula 12. The outer cannula 12 and the inner cannula 30 may be characterized by their inner diameters (referring to the diameter of the interior of the passageway) or their outer diameters (referring to the diameter as measured from the exterior outside wall to exterior outside wall).

Because the inner cannula 30 fits within the outer cannula 12, the outer cannula 12 features a larger inner diameter 70 relative to an outer diameter 74 of the inserted portion 76 of the inner cannula 30. The outer diameter 74 of the inner cannula 30 may be selected to allow sufficient air flow while also fitting comfortably within the outer cannula 12 and allowing for appropriate insertion force. The inner diameter of the inner cannula 30 is less than the outer diameter 74 by the thickness of the walls of the inner cannula 30. For example, an inner cannula 30 sized to 6.5 mm may have an outer diameter 74 of about 6.5 mm and an inner diameter of about 5.5 mm. In such an embodiment, the inner cannula walls are about 1 mm thick in the inserted portion of the inner cannula 30 (e.g., in portions distal of the compressible end region 32). Similarly, a 10 mm inner cannula 30 may have an inner diameter of about 9 mm. Accordingly, tubes sized to 6.5 mm, 7.0 mm, 7.5 mm, 8.0 mm, 8.5 mm, 9.0, or 10 mm may feature smaller inner diameters that define the airflow passage.

Further, the inner diameter 82 at the proximal end 44 of the outer cannula 12 is typically larger than the inner diameter 70 and is selected to couple to appropriate tubing. That is, the outer cannula 12 is narrower in the inserted portion and is wider at the connector. The inner cannula connector 36 also has a larger outer diameter 84 relative to the inserted portion 76. In certain embodiments, the inner cannula connector 36 may flare or taper outwards gradually such that the diameter increases gradually, with the largest diameter 84 at the proximal end 34. In other embodiment, the inner cannula connector 36 32 may include a generally barrel-shaped region with an outer diameter 84.

An operator may apply a biasing force (see arrow 42) to opposing sides of the compressible portion 40 during insertion of removal of the inner cannula 30. For example, an insertion force along arrow 58 may be accompanied by a simultaneous compression of the compressible portion 40. In certain embodiments, as the distal end 56 passes through the compressible portion 40, the biasing force is along a plane generally orthogonal to the direction of insertion. While the depicted embodiment shows compression along the lateral plane (i.e., relative to a ventral-dorsal plane), it should be understood that the compression force may be applied at other points about the compressible portion 40.

FIG. 4A is a cross-section of the outer cannula connector 28 showing the compressible portion 40 in an uncompressed configuration. In one embodiment, the uncompressed configuration is a default or unbiased configuration. The compressible portion 40 may form an annular shape, including a circle or elliptical shape, when uncompressed. In the depicted embodiment, both the exterior circumference 96 and the interior passage 98 are generally circular. It certain embodiments, the cross-sectional shape formed by the exterior circumference 96 may be different than the cross-sectional shape formed by the walls 97 of interior passage 98 and may depend on the shape and/or thickness of the walls 97. For example, the exterior circumference 96 of the compressible portion 40 may be generally elliptical while the interior passage 98 may be generally circular. The diameter 100 of the interior passage 98 in the uncompressed configuration may be selected to conform to the desired inserted portion 76 of the inner cannula 30 (see FIG. 3). That is, the diameter 100 may be slightly larger than the corresponding inner cannula outer diameter 74.

FIG. 4B shows the compressible portion 40 after application of a biasing force along arrows 42. When force is applied, the sides 90a and 90b of the compressible portion 40 move towards one another as the compressible portion 40 assumes the compressed configuration. For example, an application of 5N of force or less may be applied to achieve sufficient compression to insert the inner cannula 30. The biasing force results in deformation of the compressible portion 40 and a change in the cross-sectional shape formed by both the exterior circumference 96 and the interior passage 98. As depicted, both the exterior circumference 96 and the interior passage 98 are flattened to be more elliptical and less circular. Further, rather than a single diameter 100, the interior passage 98 may be characterized by a minor diameter 102 and a major diameter 104. The relationship between the uncompressed diameter 100 and the major diameter 104 and minor diameter 102 of the compressed configuration may be determined by the materials from which the compressible portion 40 is formed. That is, the spring force of the material may influence the amount of deformation. In addition, the coupling between the compressible portion 40 and the adjacent portions of the outer cannula connector 28 may also influence the amount of deformation. For example, a compressible portion 40 that includes a compressible ring not directly or flexibly coupled to the outer cannula connector 28 may be characterized by the ability to deform equally at any point along the ring. Such a structure may have more degrees of freedom and may compress differently than a compressible portion that includes a compressible ring that is directly coupled to one or more adjacent rigid elements at certain points along the ring. For such a structure, compression may resemble flattening in one direction. Accordingly, although the resulting compressed structure may be generally elliptical, the ellipse may be irregular.

Further, deformation of the compressible portion 40 may occur with or without an inserted inner cannula 30. In embodiments in which the inner cannula 30 is inserted, abutment of the interior surface 106 of the compressible portion against the inner cannula may halt further compression by an operator. Accordingly, during insertion, the operator may adjust the level of compression according to feel and judgment. That is, as the proximal end 54 enters the compressible portion 40, any difficulty in inserting the inner cannula 30 may be alleviated by decreasing the amount of biasing force applied until the appropriate insertion force is achieved. In addition, the dimensions of the interior passage 98 and the outer diameter of the inner cannula 30 may form part of the coupling. For example, the inner cannula 30 may be sized to form a compression fit with the inner cannula connector 28 when inserted and the compressible portion 40 is uncompressed.

Figure 5B:
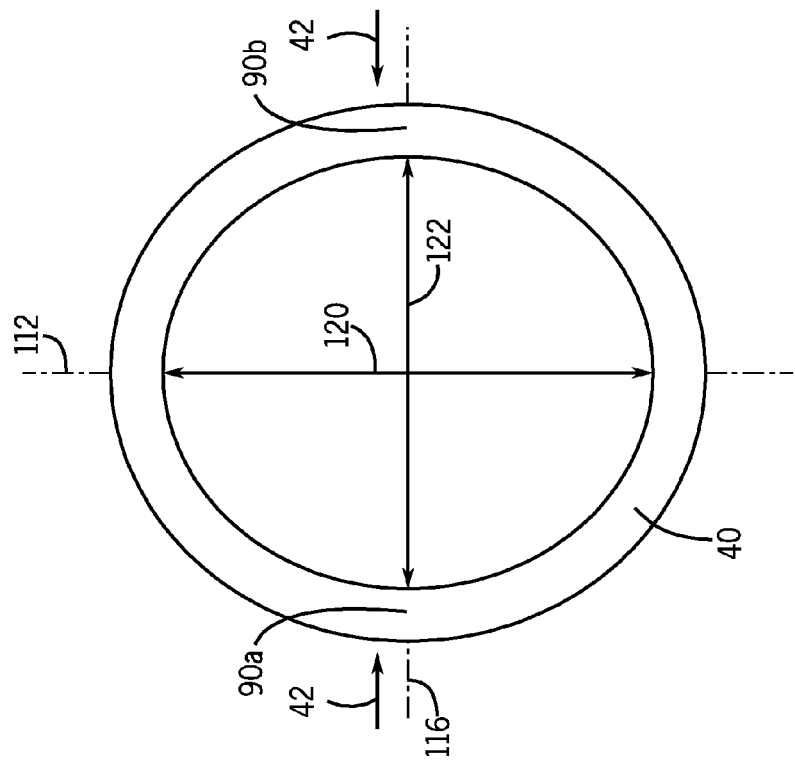
FIG. 5B shows the compressible portion of FIG. 5A in the compressed configuration.
Figure 5A:
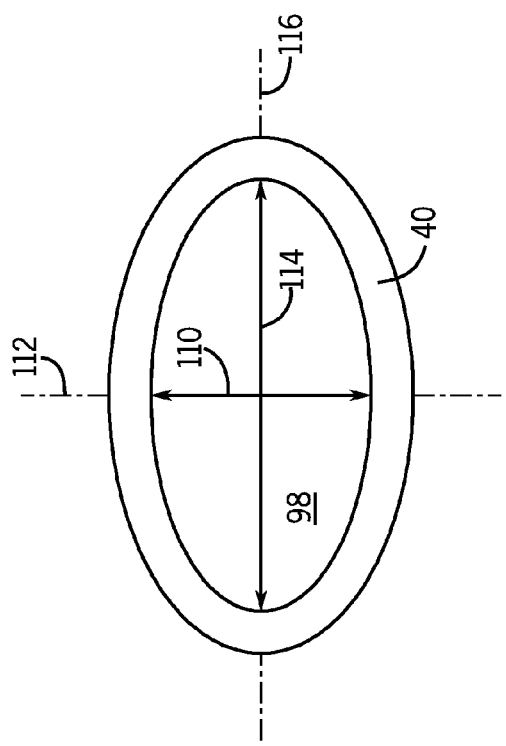
FIG. 5A is a cross-sectional of an alternative embodiment of a compressible portion of the tracheal tube of FIG. 3 in an uncompressed configuration.

FIG. 5A is view of a cross-section of an alternate embodiment of a compressible portion 40 having a generally elliptical shape and defining a generally elliptical passageway 98 in an uncompressed configuration. The compressible portion 40 features a minor diameter 110 along a first axis 112 and a major diameter 114 along a second axis. As shown in FIG. 5B, upon compression along the axis 116 of the major diameter 114, shown by arrows 42), the sides 90a and 90b move towards each other and the diameter 122 between them decreases relative to the uncompressed diameter 114 along the same axis. In the depicted embodiment, the ellipse becomes more circular when compressed in the direction shown. In addition, the diameter 120 along the first axis 112 increases relative to the uncompressed diameter 110 along the same axis. In certain embodiment, the diameter 122 is between 90-95%, between 80-90%, or at least 70% of the uncompressed diameter 114. Similarly, the diameter 112 is between 90-95%, between 80-90%, or at least 70% of the diameter 120.

FIG. 6A illustrates a cross-section of a compressible portion 40 with an inserted inner cannula 30. In particular embodiments, the compressible portion 40 may include mating features on the interior wall 106 that couple to complementary features on the exterior surface 144 of the inner cannula 30. Such mating features may form part of a release grip formed by the compressible portion 40. Further, the mating features may prevent rotational movement of the inner cannula 30 relative to the outer cannula connector 28. In addition, the mating features may provide additional alignment to facilitate correct alignment of the curve of the inner cannula 30 with the curve of the outer cannula 12 (see FIG. 3). It should be understood that the positions of the mating features may be exchanged. That is, in certain embodiments, one or more of the disclosed protrusions may be exchanged with recesses and vice versa. In addition, the inner cannula 30 and/or the compressible portion 40 may include combinations of recesses and protrusions. As depicted, the mating features may be protrusions, such as one or more protrusions 150 formed on the exterior surface 144 of the inner cannula 30 and configured to mate with recesses 152 on the compressible portion 40. The protrusion 150 may be formed in any suitable shape or combination of shapes, such a rounded bump, a ramp shape, a pyramid structure, etc. Further, the compressible portion 40 and/or the inner cannula 30 may include any number of mating features positioned about a circumference. For example, the compressible portion 40 may include two recesses 152 that oppose one another. In specific embodiments, opposing recesses 152 may be spaced at positions corresponding to dorsal and ventral sides of the patient, i.e., the inner curve 22 and the outer curve 24 of the outer cannula 12. In addition, the recesses may be spaced 90 degrees apart from a major axis in the uncompressed configuration. In another embodiment, respective protrusions 150 and/or recesses 152 may be provided as a partial ring with an arc having less than 45° of circumference of the compressible end region 32. In another embodiment, the protrusion 150 may form a complete ring about the circumference of the exterior surface 144 of the inner cannula 30.

The size of the protrusions 150 may be selected to fit into the corresponding recess 152 in the compressible portion 40 and may be less than a thickness of the wall of the compressible portion 40. In one embodiment, the protrusion 150 may protrude less than about 1 mm, less than about 1.5 mm or less than about 2 mm from the exterior surface 144. In particular embodiments, the protrusions 122 protrude less than a widest exterior diameter 162 of the compressible portion 40 in an uncompressed configuration. Alternatively, the protrusion 150 may fit into complementary windows formed in the compressible portion 40. In such embodiments, the protrusion 150 may be larger. In addition, the inner cannula 30 may feature regions of varying outer diameters that form a slope that is sized at its widest point to fit a major interior diameter 164 in the uncompressed configuration. The slope may be formed proximate to the protrusion 150 to facilitate insertion of the relatively larger protrusion 150 into the inner cannula connector 28. In addition, the major interior diameter 164 may be selected to leave lateral gaps 170 between the exterior surface 144 of the inner cannula 30 and the In operation, deformation or compression of the compressible portion 40 along arrows 42 results in the recesses 152 moving away from the protrusions 150 to allow the protrusions clearance with the interior passageway. This facilitates insertion and removal in the compressed configuration and retention in the uncompressed configuration. Accordingly, the size and shape of the interior passageway 98 may be selected so that the size of the lateral gaps 170 is sufficient to allow the appropriate amount of deformation and clearance of the protrusions 150 within the passageway 98. Further, in certain embodiments, the position of the protrusions 150 and the lateral gaps 170 may be exchanged. In the illustrated embodiment, the operator biasing force is applied laterally, which may be a relatively easy position for the patient or caregiver to apply force to an inserted tracheal tube assembly 10.

Figure 7:
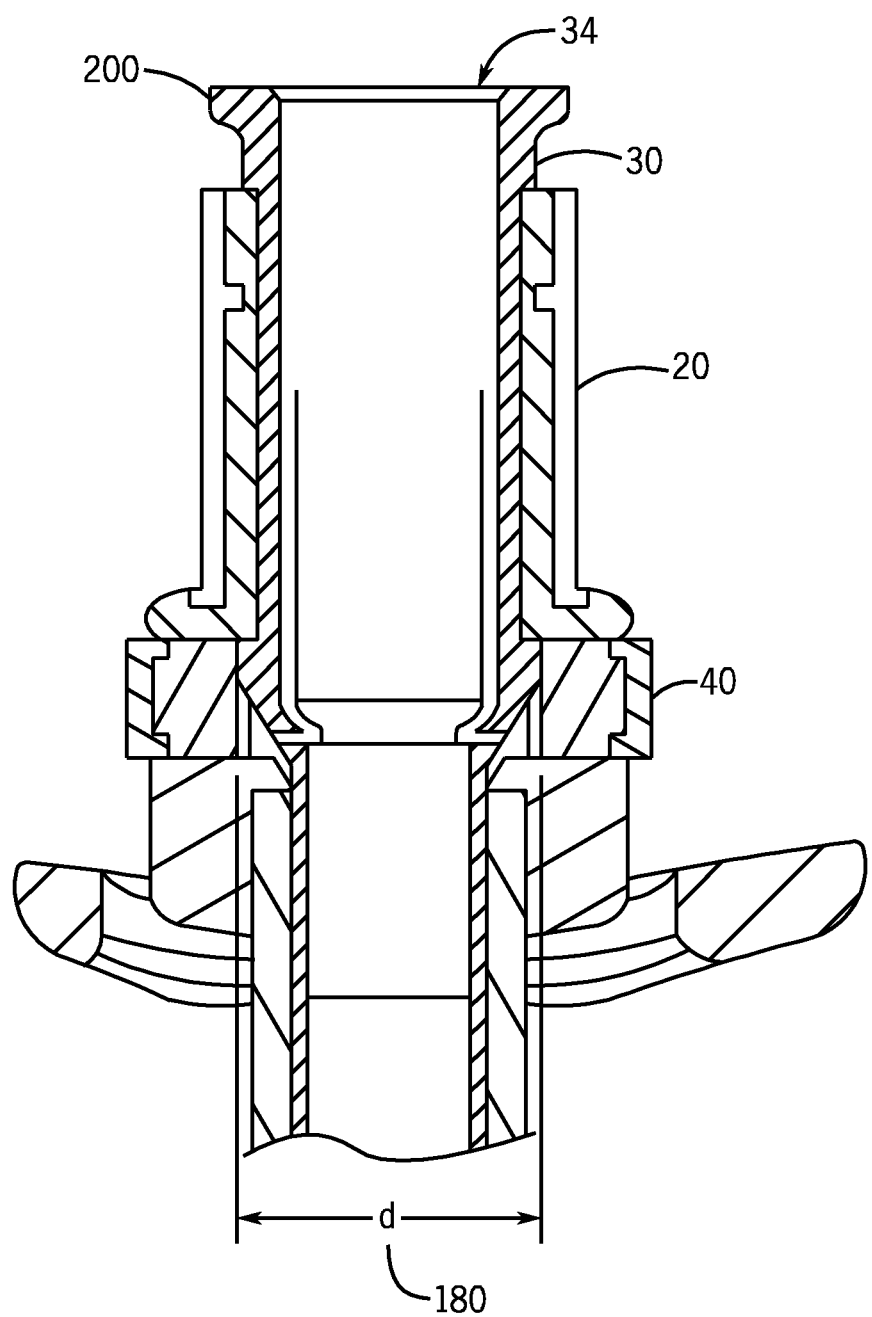
FIG. 7 is a cross-sectional view of the inner cannula connector of the tracheal tube of FIG. 3.

Further, it should be understood that the size and shape of the compressible portion 40 relative to the other portions of the outer cannula connector 28 may be selected to facilitate retention and/or sealing of the inner cannula 30 and the outer cannula connector 28. FIG. 7 is a cross-sectional view of the inner cannula connector 28 illustrating that the compressible portion 40 maintains an interior diameter 180 slightly larger than the interior diameter along the rest of the outer cannula connector 28 in the uncompressed configuration while maintaining contact with at least a portion of the inner cannula connector 40 at the illustrated points. In addition, the proximal end 34 may also terminate in a lip 200. The relatively thicker lip 200 may terminate in an abutment surface configured prevent further movement of the inner cannula 30 distally, which may assist in aligning the inner cannula 30 within the outer cannula 12.

As noted, the proximal end 34 of the inner cannula 30 is positioned outside of the outer cannula connector 28, which facilitates operator manipulation of the inner cannula 30. The proximal end 34 may include additional gripping features, such as ribs, scallops, or nubs to facilitate operator manipulation. Further, the inner cannula 30 may be formed form a material that is relatively rigid or compressible.

FIG. 8 is an exploded view of a tracheal tube assembly including an inner cannula, an outer cannula connector 28, a flange member 20, an outer cannula 12, and an inflatable cuff 16. In the depicted embodiment, the outer cannula connector includes a proximal coupler 46 that is adjacent to the compressible portion 40. The proximal coupler has materials that are less deformable or compressible that those forming the compressible portion 40. In certain embodiments, the proximal coupler 46 is manufactured from materials that are relatively rigid (i.e., not substantially deformed) when compression forces of 5N or less are applied. The compressible portion 40 also includes a conformable cover component 250 and a ring component 252. In one embodiment, the ring component 252 may be formed from a hard but flexible molded piece (e.g., via injection molding) while the cover component may be formed from a relatively softer TPE injection molding. In certain embodiments, the ring component may be a spring or may be a material with shape memory and may be formed from a variety of materials or combinations of materials that provide the desired deformation properties under operator-applied forces. For example, in certain embodiments, the ring component 250 is constructed from metal or polymeric materials (polypropylene, ABS).

In one embodiment, the ring component 252 may be injection molded in an open position as two semi-circles joined by a living hinge. During assembly, the ring component 252 is coupled via snap fit components 256 to a hub 260 that extends from the flange 20, which also maintains the ring component in the closed position. The hub 260 may include receiving features for the snap fit features that maintain the ring component 252 in the desired position. These receiving features may be sealed during assembly to prevent leaks in the ventilation circuit. The cover component 250 provides a comfortable exterior surface for patient comfort. In one embodiment, the cover component 250 is molded over the ring component 252, which in turn may couple the compressible portion 40 to the proximal coupler 46. The compressible portion 40 is coupled to the distal portions of the outer cannula 12 via the hub 260. In another embodiment, rather than employing snap fit couplings, the compressible portion may be coupled to both adjacent portions of the outer cannula connector via the overmolded cover component 250.

Components of the tube assembly 10 may be manufactured according to suitable techniques. For example, the inner cannula and/or outer cannula 12, including the outer cannula connector 28, may be molded, overmolded, two shot molded, computer numerical control (CNC) machined, milled, or otherwise formed into the desired shape. In one embodiment, a mold or mold form may be used to manufacture the inner cannula 30. In one embodiment, the mold or other manufacturing technique may facilitate a speckled outer surface of the inner cannula 30, which may facilitate insertion. One or more components may be manufactured of materials such as a polyethylene (e.g., low density polyethylene), polypropylene, PTFE, expandable PTFE, polyvinyl chloride (PVC), a PEBAX silicone, a polyurethane, thermoplastic elastomers, a polycarbonate plastic, a silicon, or an acrylonitrile butadiene styrene (ABS). In particular embodiments, the material of the inner cannula 30 may be selected to be 60 Shore D. Further, the ring component 252 may be formed from materials selected to be 70 Shore A while the cover component 250 may be formed from polyurethane selected to be 35-45 Shore A.

It is envisioned that the tracheal tube assembly 10 as provided herein may be provided as an assembly and/or as a kit. A kit may include a packaging that encloses an inner cannula 30 sized for an outer cannula 12. The kit may also include a neck strap for retaining the tracheal tube 10 in place. The kit may also include an obturator. Other components of the kit may include a cap configured to be placed on a proximal end 34 while the obturator is in use and that may be part of the obturator. The tube assembly 10 components (e.g., outer cannula 12, flange member 20, outer cannula connector 28, cuff 16, and pilot balloon assembly 18) may be assembled prior to in situ assembly of the inner cannula 30 into the outer cannula 12. Indeed, the user or clinician may perform final assembly of the tracheal tube 10 by selecting a desired inner cannula 30 from a selection of inner cannulas and then inserting the inner cannula 30 into the outer cannula 12 prior to intubation. Thus assembled, the tracheal tube 10 may then be inserted into the patient's trachea.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to airway devices, but these techniques may also be utilized for connections between inner and outer conduits for other types of medical devices and medical connective tubing. Rather, the various embodiments may cover all modifications, equivalents, and alternatives falling within the spirit and scope of the disclosure as defined by the following appended claims.

What is claimed is:

1. A tracheal tube assembly comprising:
    an outer cannula configured to be positioned in a patient airway;
    a flange member secured about the outer cannula;
    an outer cannula connector coupled to a proximal end of the outer cannula, wherein the outer cannula connector comprises a proximal rigid portion and a distal compressible portion, wherein compression of the distal compressible portion results in a larger inner diameter of the compressible portion in at least one dimension;

an inner cannula configured to be disposed inside the outer cannula such that the inner cannula and the outer cannula are coaxial; and an inner cannula connector coupled to the inner cannula and configured to be disposed in the outer cannula connector.

2. The tracheal tube assembly of claim 1, wherein the distal compressible portion comprises one or more mating features disposed on an interior surface and configured to mate with one or more complementary features on the inner cannula connector.

3. The tracheal tube assembly of claim 2, wherein the one or more mating features comprise a recessed annulus.

4. The tracheal tube assembly of claim 3, wherein the one or more complementary features comprise a protruding ring.

5. The tracheal tube assembly of claim 3, wherein the one or more complementary features comprise opposing protrusions.

6. The tracheal tube assembly of claim 2, wherein the one or more mating features comprise a protruding annulus.

7. The tracheal tube assembly of claim 6, wherein the one or more complementary features comprise a plurality of protrusions.

8. The tracheal tube assembly of claim 2, wherein the one or more complementary features comprise a tapered region having a varying exterior diameter.

9. The tracheal tube assembly of claim 1, wherein the distal compressible portion is elliptical in shape having a minor axis that extends from a ventral side to a dorsal side of the tracheal tube assembly when the tracheal tube is inserted in the patient and a major axis that extends laterally.

10. The tracheal tube assembly of claim 9, wherein the minor axis, from exterior surface to exterior surface, is larger than an exterior diameter of the proximal rigid portion.

11. The tracheal tube assembly of claim 1, wherein an exterior circumference of the distal compressible portion is larger than an exterior circumference of the proximal rigid portion.

12. The tracheal tube assembly of claim 1, wherein the distal compressible portion is adjacent to the rigid proximal portion.

13. The tracheal tube assembly of claim 1, wherein the outer cannula connector comprises a distal rigid portion coupled to a distal end of the distal compressible portion and to the flange member.

14. The tracheal tube assembly of claim 1, wherein the distal compressible portion comprises a compressible annulus member covered by a resilient material.

15. The tracheal tube assembly of claim 1, wherein the distal compressible portion comprises a shape memory material.

16. The tracheal tube assembly of claim 1, wherein the distal compressible portion is configured to assume a compressed configuration under pressure, wherein the compressed configuration comprises a decrease in a first diameter along a first axis and an increase in a second diameter along a second axis.

17. A tracheal tube assembly comprising:
an outer cannula configured to be positioned in a patient airway;
a flange member secured about the outer cannula;
an outer cannula connector coupled to a proximal end of the outer cannula, wherein the outer cannula connector comprises a compressible portion disposed between the flange member and a rigid proximal portion, wherein the compressible portion is configured to be in an uncompressed configuration when unbiased and a compressed configuration when force is applied;
an inner cannula configured to be disposed inside the outer cannula such that the inner cannula and the outer cannula are coaxial; and
an inner cannula connector coupled to the inner cannula and configured to be disposed in the outer cannula connector.

18. The tracheal tube assembly of claim 17, wherein the uncompressed configuration and the compressed configuration both are elliptical in shape about their respective outer circumferences.

19. The tracheal tube assembly of claim 18, wherein a major axis of the uncompressed configuration is orthogonal to a major axis of the compressed configuration.

20. The tracheal tube assembly of claim 17, wherein a smallest inner diameter in the uncompressed configuration is less than a smallest inner diameter in the compressed configuration.

21. The tracheal tube assembly of claim 17, wherein the inner diameter of the rigid portion is substantially the same under a biasing force that reversibly compresses the compressible portion.

22. The tracheal tube assembly of claim 17, wherein the inner diameter of the rigid portion changes less than 1% under a biasing force that reversibly compresses the compressible portion.

* * * * *